(12) United States Patent
Tan et al.

(10) Patent No.: US 8,486,034 B2
(45) Date of Patent: Jul. 16, 2013

(54) METHOD AND DEVICE FOR EXTRACTING AND/OR COLLECTING BLOOD FROM PLACENTA AND/OR UMBILICAL CORD

(75) Inventors: Kok Kiong Tan, Singapore (SG); Sunan Huang, Singapore (SG); Kok Zuea Tang, Singapore (SG); Soon Chye Ng, Singapore (SG)

(73) Assignee: National University of Singapore, Singapore (SG)

( * ) Notice: Subject to any disclaimer, the term of this patent is extended or adjusted under 35 U.S.C. 154(b) by 994 days.

(21) Appl. No.: 11/792,114

(22) PCT Filed: Dec. 1, 2005

(86) PCT No.: PCT/SG2005/000410
§ 371 (c)(1),
(2), (4) Date: Jun. 1, 2007

(87) PCT Pub. No.: WO2006/059958
PCT Pub. Date: Jun. 8, 2006

(65) Prior Publication Data
US 2009/0035845 A1 Feb. 5, 2009

(30) Foreign Application Priority Data

Dec. 1, 2004 (SG) .................................. 200407049

(51) Int. Cl.
*A61M 1/00* (2006.01)
(52) U.S. Cl.
USPC ....................................... 604/317; 435/287.1
(58) Field of Classification Search
USPC .... 604/317–323, 403, 409, 540, 541; 494/42, 494/37; 606/119, 120; 435/287.1; 128/897
See application file for complete search history.

(56) References Cited

U.S. PATENT DOCUMENTS 4,335,040 A * 6/1982 Livingston .................... 530/427
4,769,001 A * 9/1988 Prince .......................... 604/6.07
(Continued)

FOREIGN PATENT DOCUMENTS

WO   WO 98/07460   2/1998
WO   WO 98/07461   2/1998
(Continued)

OTHER PUBLICATIONS

International Search Report for International Appl. No. PCT/JPSG2005/000410, Australian Patent Office, mailed on Feb. 2, 2006.
(Continued)

*Primary Examiner* — Tatyana Zalukaeva
*Assistant Examiner* — Benedict L Hanrahan
(74) *Attorney, Agent, or Firm* — Hamilton, Brook, Smith & Reynolds, P.C.

(57) ABSTRACT

A device for extracting and collecting blood from a delivered placenta comprising a compartment to contain and support a delivered placenta and umbilical cord. The compartment includes a flexible membrane which can be displaced (preferably under the influence of a fluid (preferably gas) pressure differential between the compartment side and non compartment side of the membrane) to impart onto the placenta a pressure to encourage the displacement of fluid carried by the placenta towards the umbilical cord. The compartment includes at least one outlet opening via which the umbilical cord can extend (preferably in a sealed manner) to allow the flexible membrane pressure induced flow of fluid carried by the placenta to displace from the compartment for external to the compartment collection of the fluid.

23 Claims, 11 Drawing Sheets

Side view

U.S. PATENT DOCUMENTS

| | | | |
|---|---|---|---|
| 5,053,025 A * | 10/1991 | Knippscheer | 604/317 |
| 5,342,328 A | 8/1994 | Grossman et al. | |
| 5,915,384 A * | 6/1999 | Grossman et al. | 600/573 |
| 6,491,682 B2 * | 12/2002 | Paderni | 604/541 |

FOREIGN PATENT DOCUMENTS

| | | |
|---|---|---|
| WO | WO 98/46151 | 10/1998 |
| WO | WO 2004/080304 | 9/2004 |

OTHER PUBLICATIONS

Bertolini F. et al. "Comparative study of different procedures for the collection and banking of umbilical cord blood", J. Hematother, 1995:4:29-36.

McCullough J. et al. "Factors influencing the availability of umbilical cord blood for banking and transplantation", Transfusion, 1998:38:508-510.

* cited by examiner

METHOD AND DEVICE FOR EXTRACTING AND/OR COLLECTING BLOOD FROM PLACENTA AND/OR UMBILICAL CORD

BACKGROUND OF THE INVENTION

1. Field of the Invention

The present invention relates to a method and device for extracting and/or collection of biological fluid from animal organs. In particular, the present invention relates to an umbilical cord blood extraction and/or collection method, device and/or system. In particular the invention generally relates to a device for extracting and/or collecting of umbilical cord blood to yield useful volumes of blood from a delivered placenta and/or umbilical cord.

2. Background of the Invention

It is well known that umbilical cord blood or UCB, is an increasingly important and rich source of stem cells. It is known that stem cells can divide to create new red blood cells which carry oxygen to the brain, new white blood cells used in a bodies immune system and new platelets which can assist in blood clotting. It is currently estimated that stem cells can be used for the treatment of over 45 malignant and non-malignant diseases. Such may include certain cancers such as leukaemia and immune and genetic disorders.

UCB may also provide a readily available source of stem cells for transplantation in many situations where bone marrow is currently used. Hence the use of UCB instead of other sources of stem cells such as for example bone marrow and peripheral blood has many advantages. Such may include for example the reduction or elimination of risk involved in the collection of UCB.

UCB is also easier to collect and harvest without the risks associated with general anaesthesia required for the purposes of extracting bone marrow. UCB is also readily available when needed if it is properly collected and stored at birth. It has been found that UCB is also more often compatible to a person when used in transplants. Furthermore UCB has a lower procurement cost. It has also been demonstrated that UCB has broader potential clinical applications for improving neural repair and bone and tissue growth.

As such the importance of UCB is now widely recognised. Blood centres worldwide may collect and store UCB after delivery of a baby subject to the parents consent or request. The UCB may become extremely useful and indispensable at a later stage in life in saving the life of the new born baby. However one problem associated with UCB is that its collection appears to be a one time possibility and the amount of blood that can be collected is limited using current blood collection technology. Such current blood collection technology may include syringe assisted and gravity assisted methods.

A few studies have been conducted including for example that published by Bertolini F., Lazzari L., Lauri E. et al. *Comparative study of different procedures for the collection and banking of umbilical cord blood*. J Hematother 1995:4: 29-36. Such methods are manually carried out. As well as the task being tedious and difficult to achieve the current ways of extracting the blood also creates inherent risk of unnecessary contamination.

According to McCullough J., Herr G., Lennon S. et al. *Factors influencing the availability of umbilical cord blood for banking and transplantation*. Transfusion 1998:38:508-510, the current ways of UCB collection typically recovers 20-40 ml. Apart from obstetric factors such as infant weight and time of collection, the procedure involved and the equipment used to perform the collection influence the final yield.

There is therefore a need in the art for an umbilical cord blood collection apparatus which can effectively yield an increased volume of blood from a delivered placenta when compared to some of the prior art known.

BRIEF SUMMARY OF THE INVENTION

The present invention provides a method of extracting and/or collecting biological fluid from a delivered placenta and/or umbilical cord, the method comprising: providing a delivered placenta and/or umbilical cord; and applying pressure to the placenta and/or umbilical cord, thereby extracting and/or collecting the biological fluid.

The present invention also provides a method comprising the steps of: —providing a delivered placenta and/or umbilical cord; —placing placenta and/or umbilical cord in a compartment of a device; connecting umbilical cord to a collection means; and applying pressure to the placenta and/or umbilical cord, thereby extracting and/or collecting the biological fluid, wherein the biological fluid is blood. The method further comprises holding the placenta or umbilical cord to prevent slippage.

Further, the applying pressure is achieved by means of fluid pressure; the fluid is air or a gas the fluid is a liquid.

According to the method of the present invention, the applying pressure is applied to the placenta in a direction from the periphery to the centre of the placenta. Alternatively, or in addition, the pressure may be applied to the umbilical cord in a direction from the maternal end to the fetal end.

The present invention provides a device for extracting and/or collecting biological fluid from a delivered placenta and/or umbilical cord, the device comprising: a compartment to contain and/or support the placenta and/or umbilical cord; and a fluid collection means and the compartment may be funnel shaped.

The device further comprising a pressure transmitting means and a holding means to prevent slippage of the placenta and/or umbilical cord. The pressure transmitting means comprises a pressure pad that comprises an integral sealing ring, has variable thickness and/or is thicker at the edges than at the centre.

The device may comprise a pressure application lid connectable to the compartment, the pressure application lid comprising at least one inlet interface to a pressure source. The pressure source may be a compressed gas tank, a gas line or a liquid source. The lid may at least one interface to a pressure gauge and/or a outlet interface and the outlet interface is connected to a vacuum pump.

The fluid collection means of the device may further comprise a umbilical cord positioner and/or a venturi, and the venturi any further comprise absorbent material. The fluid collection means further comprises at least one tubular needle for insertion into at least one blood vessel in the umbilical cord and/or a collection vessel which may have a pressure less than atmospheric pressure.

The device may further comprise means for applying vibration to the placenta and/or umbilical cord using a vibrator and the compartment of the device may be located higher than the fluid collection means.

The present invention also provides a system to extract and/or collect biological fluid from a delivered placenta and/or umbilical cord, the system comprising an extraction and/or collection device described in the paragraphs above and a control means. The control means comprises at least one computing device with control software; and at least one electromechanical device for controlling inlet air into a pressure application lid. The control means further may further comprise at least one electromechanical device for sensing air pressure within the pressure application lid and/or at least one electromechanical device for releasing pressure within the pressure application lid. The control means may further comprise at least one control means for a vibrator and the control software may have an open architecture.

DETAILED DESCRIPTION OF THE INVENTION

The present invention relates to a method, device and/or system to extract and collect biological fluids from organs. In particular, the present invention relates to a method for the extraction and/or collection of umbilical cord blood from a delivered placenta and/or umbilical cord. The device or apparatus, and a system to practise the method are also taught.

A placenta when separated or delivered from the mother, has a maternal side which was attached to the mother and a fetal side, which is the side of the umbilical cord attached to the baby. Similarly, when an umbilical cord is detached or cut from the placenta, the umbilical cord has a maternal end which is the end nearest the placenta and a fetal end, which is the end nearest the baby.

Under the present invention, the organ (in this example, the placenta and/or umbilical cord) is contained and/or supported and may be further secured or held to prevent slippage. Pressure may then be applied to the placenta in a direction from the maternal side of the placenta to the fetal side of the placenta to push blood out of the umbilical cord. This is in contrast to the methods of the prior art where the blood is either extracted by with vacuum force (eg with a syringe) alone or drained by gravity alone. In some embodiments of the invention, the placenta may be placed in a position such that the maternal surface is uppermost and the umbilical cord is below and at the centre of the placenta. In such a position, pressure is applied in a direction from the periphery of the placenta to the centre of the placenta.

If only the umbilical cord is provided, the direction of the pressure is applied from the maternal end of the cord to the fetal end of the cord.

The pressure may be provided by a fluid such as a liquid or a gas, preferably a gas such as air. The pressure is against a pressure transmitting means such as a pressure pad. Alternatively, the pressure may be applied by hand or other mechanical means such as a roller.

The blood thus extracted is collected in a vessel which may or may not be under negative atmospheric pressure. Alternatively, the blood may be collected by a tubular needle inserted into one or more blood vessels of the umbilical cord.

A preferred embodiment of the present invention is an automated system incorporating the device or apparatus of the present invention and utilizing the method of the present invention.

The preferred embodiment includes the following four primary components: a placenta tray with umbilical cord positioner which forms a first compartment, an air-tight chamber with a controlled and distributed pneumatic pressure application system, formed from the first chamber and a pressure application lid, an adjustable and integrated vibratory structure, and an open-architecture software control system fulfilling the functionalities of the overall system.

The Components

Placenta Tray and Umbilical Cord Positioner or Compartment

Figure 1:
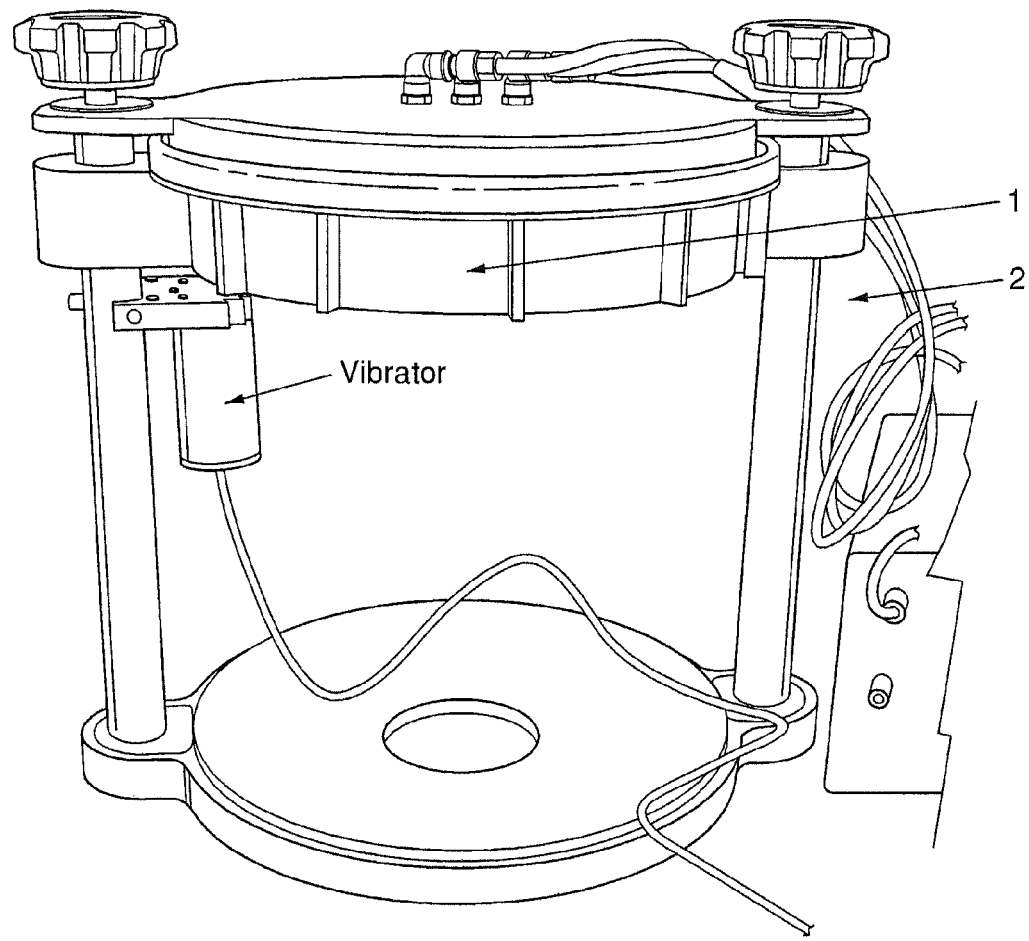
FIG. 1 is a representation of the blood collection unit in fluid communication with a controller.
Figure 2:
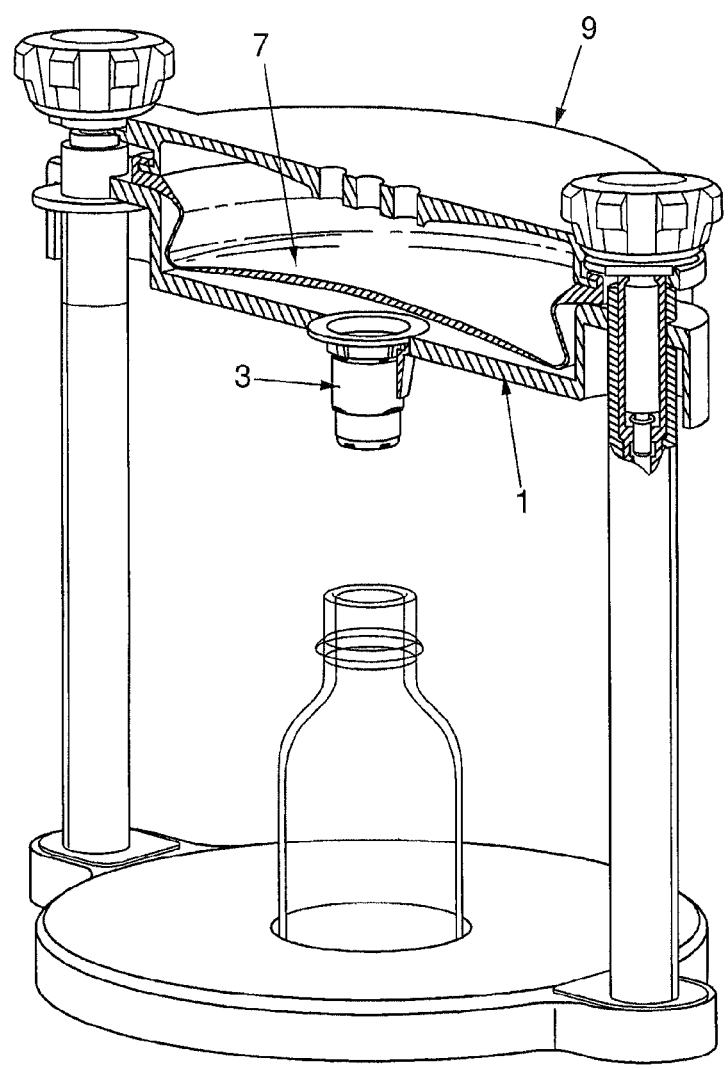
FIG. 2 is a partial sectional perspective view of the blood collection unit.
Figure 3:
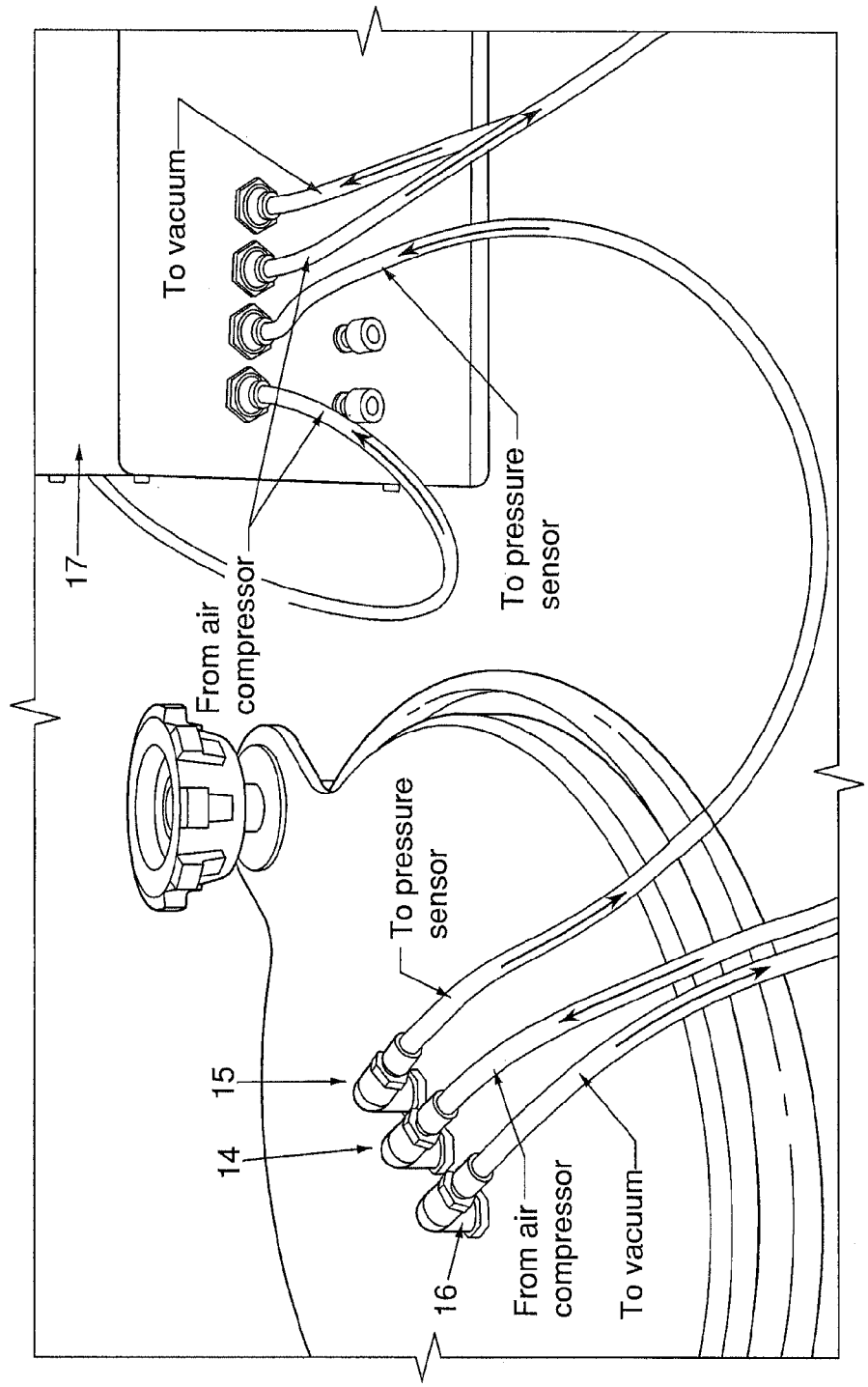
FIG. 3 is a representation of the placenta tray engaged in fluid communication with the controller.
Figure 4:
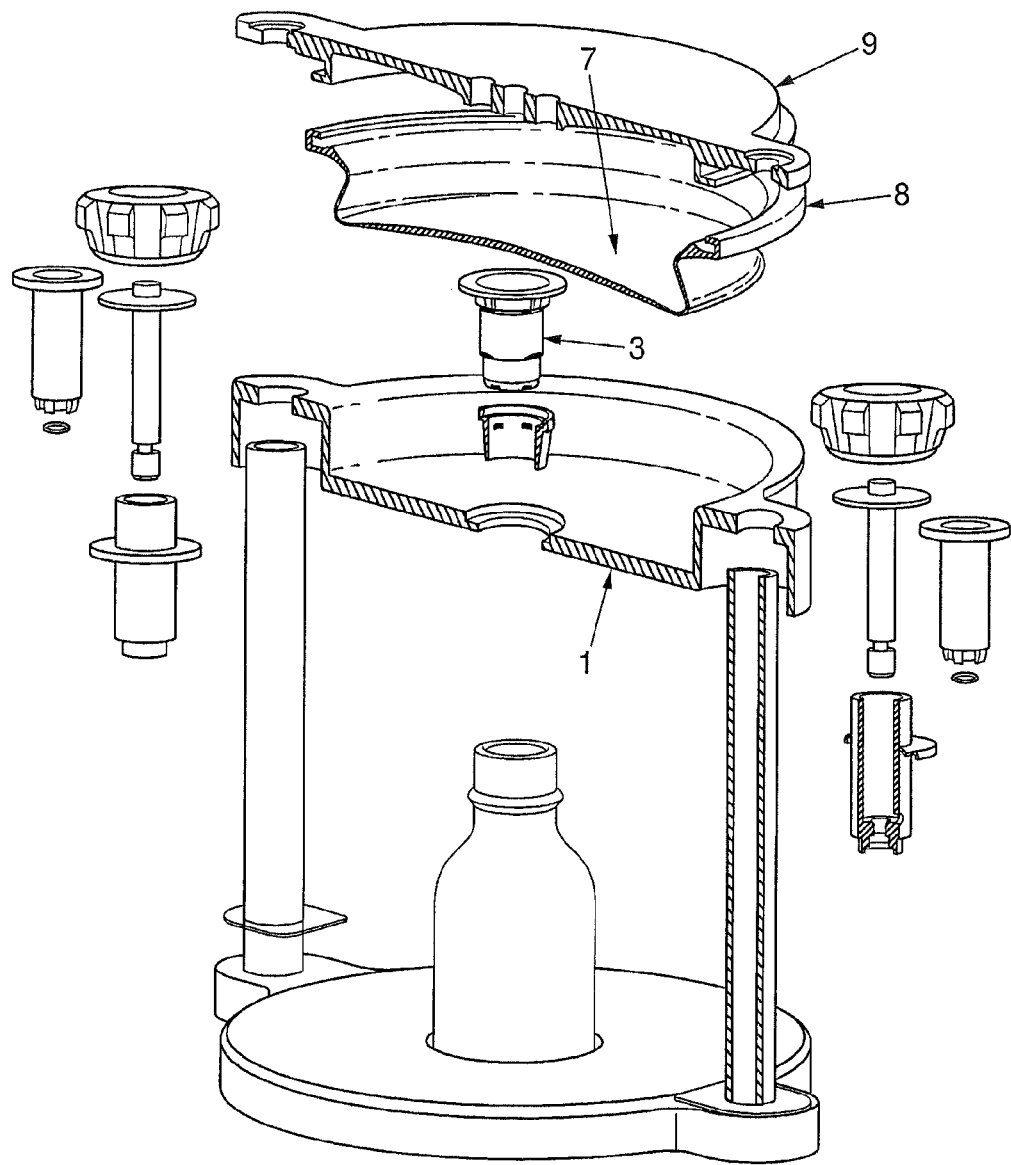
FIG. 4 is a partial sectional perspective and exploded view of the blood collection unit of FIG. 2.
Figure 5:
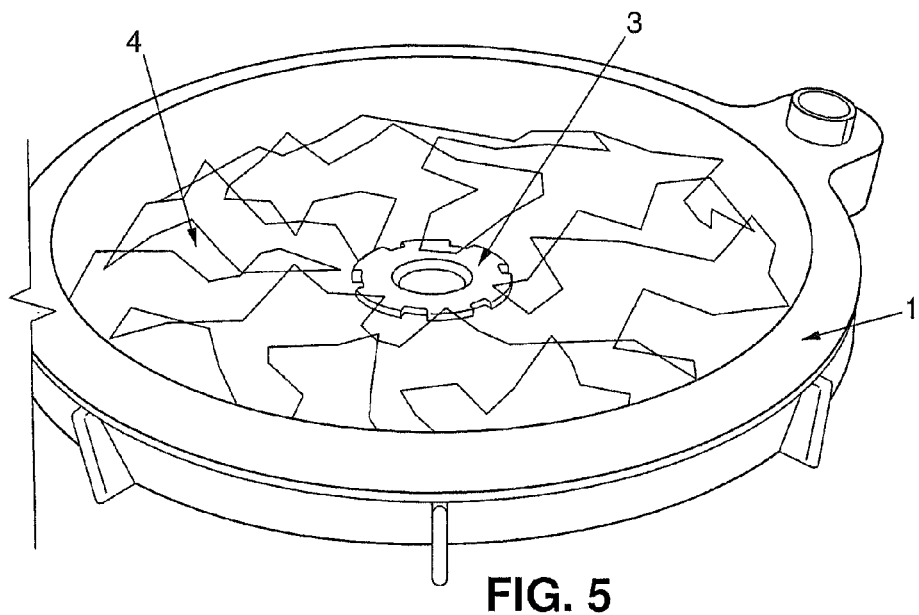
FIG. 5 is a perspective view of the placenta tray with its lid removed.
Figure 6A:
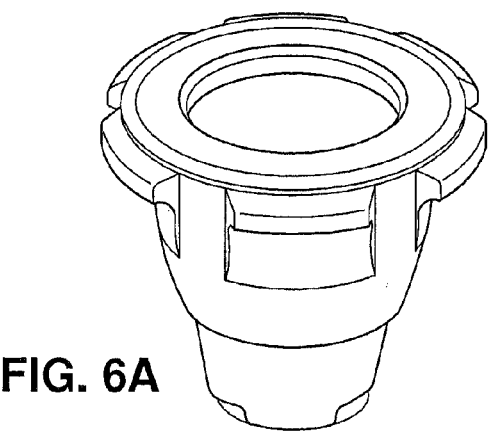
FIG. 6A is a perspective view of the placenta tray umbilical cord positioner.
Figure 6B:
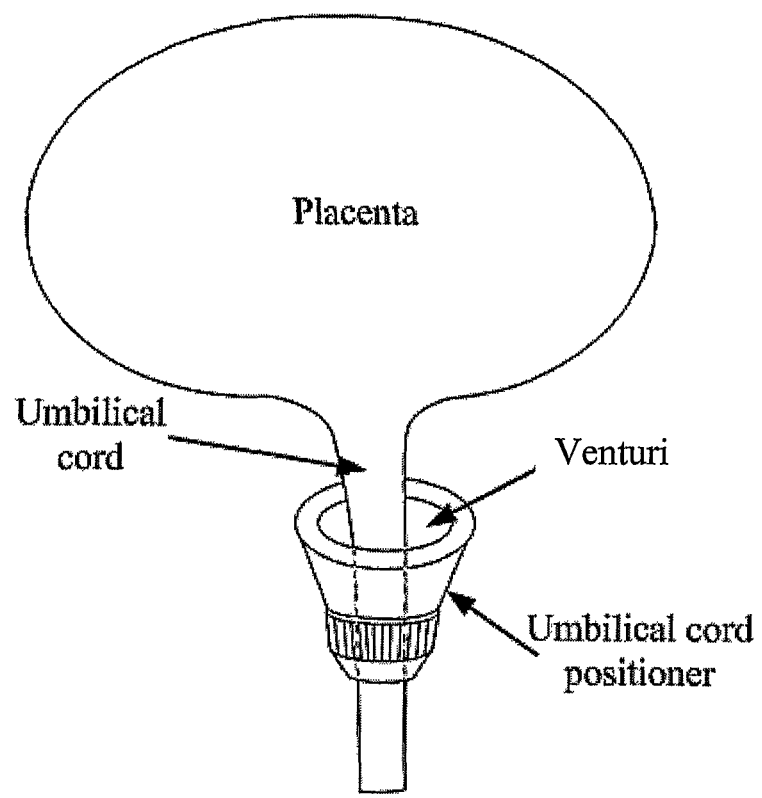
FIG. 6B is a diagrammatic view of a placenta and the umbilical cord positioner and wrapper.
Figure 7:
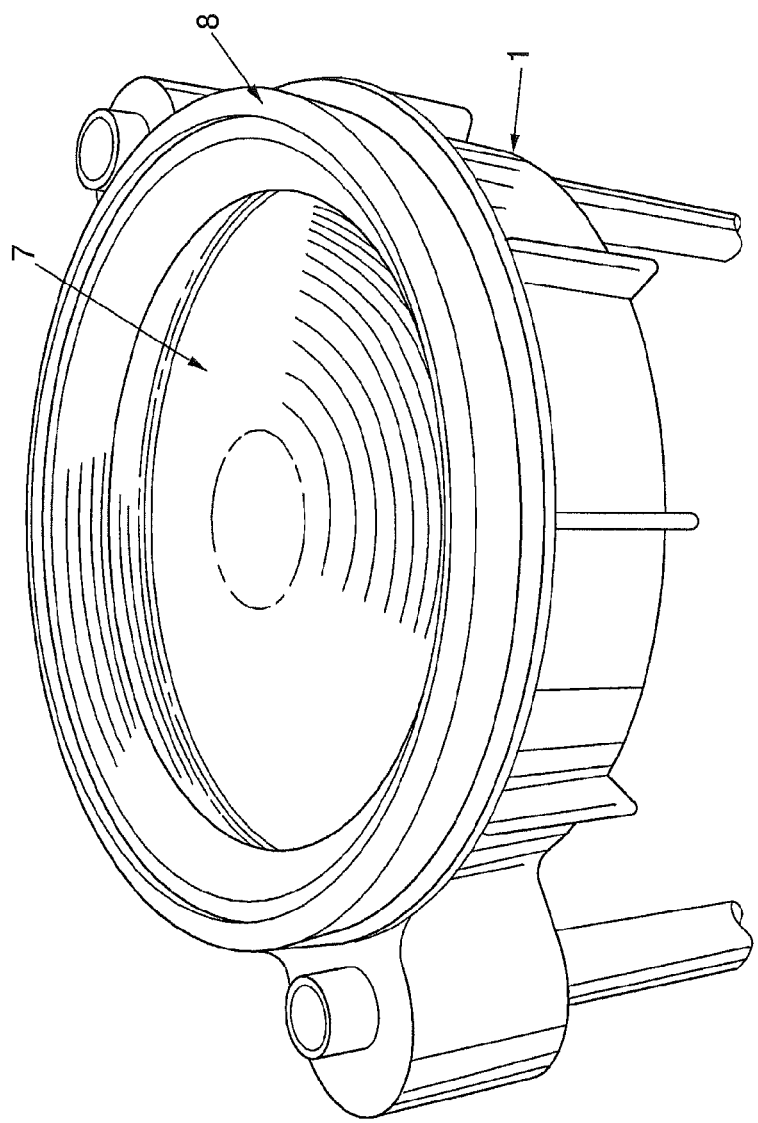
FIG. 7 is a perspective representation of the tray with its lid removed but with a cover or pressure pad located over the interior cavity of the tray.

The placenta tray 1 is preferably a modular slightly-reverse sloping (cone-shaped) component, that is, the centre of the cone is lower than the periphery of the cone. It forms part of the overall (preferably stainless steel) support structure 2. It serves as the support base for the placenta, with the maternal side facing upward, the fetal side facing downward. The umbilical cord, originating from the fetal side, passes through a venturi structure as shown in FIG. 6B of the funnel-shaped element which is formed by a plastic umbilical cord positioner 3. The venturi structure and umbilical cord positioner form part of the blood collection means. The placenta can be wrapped in a wrapper 4 prior to being placed in the tray to reduce the possibility of contamination. The umbilical cord positioner 3 is preferably walled with a disposable absorbent. The umbilical positioner includes or is walled with a disposable absorbent material to allow for any fluids running from the placenta onto the umbilical cord positioner, to be absorbed rather than having these fluids flow onto other parts of and through the venturi. The absorbent material therefore allows for the device to be kept cleaner than should there not have been any absorbent material provided. The positioner acts as a mechanical filter against contaminated blood from the surfaces of the placenta dripping through the venturi by the absorbent material absorbing the blood.

Figure 12:
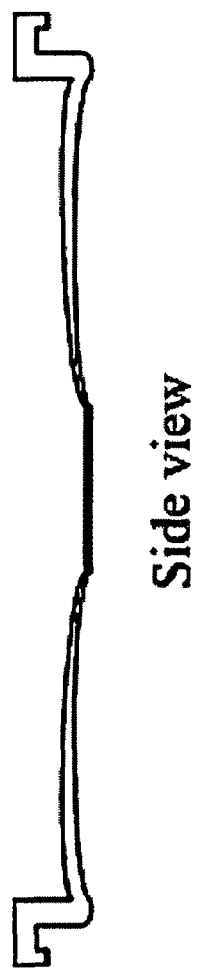
FIG. 12 is a sectional view through the pressure pad showing the preferred variation in thickness across the diameter of the pressure pad wherein the thicker part of the pressure region is provided at the circumference of the pad.

A variable thickness silicone pressure pad 7 with an integral sealing ring 8 serves as a pressure transmitting means and in the preferred embodiment, also serves as holding means to prevent slippage of the placenta. The pad can be snapped into position above the maternal side of the placenta to capture the placenta in the placenta tray. This pad fulfils a three-fold function. It serves to keep the slippery placenta in place, air-seals the gap between the pressure application lid 9 and the placenta tray base 10, and its deliberate varying thickness design will evenly distribute pneumatic pressure radially across the maternal side of the placenta from the periphery of the placenta towards the umbilical cord at the centre, when the pneumatic pressure is applied. This exerts the pressure in the overall direction from the maternal side of the placenta and umbilical cord to the fetal side. With reference to FIG. 12, it can be seen that the silicone pressure pad has a thicker wall thickness at the circumference of the pressure portion of the pad than at and towards the middle of the pressure pad. It is also not of a planar shape but has a slight double concave surface to its downward or inward side across the diameter of the pad.

Pneumatic Pressure Application System

The pneumatic pressure application system comprises of a pressure application lid 9 which is connected by snapping or securing onto the placenta tray I. Together with the placenta tray 1 and positioner 3, they form an air-tight chamber 13. The sealing ring 8 which is an integral part of the pressure pad 7 is used to eliminate air-leakage. The lid 9 houses three interfaces to standard air tubings. One interface 14 is connected to an air tubing via a servo valve from a compressed air source which can be an air cylinder or an air line connected to an air compressor (not shown). The second interface 15 is connected to a pressure sensor inside the box 17 to yield chamber pressure measurements and to complete the control loop. The actual chamber pressure can be varied to follow a desired profile by manipulating directly the valve opening via a pressure controller. In this way, a massaging action is delivered to the placenta to induce a faster and smoother flow of blood from the placenta. The third interface 16 is connected to a vacuum pump to speed up the exhaust process to equilibrate the air pressure of the chamber with atmospheric pressure.

Vibratory Structure

The stainless steel structure is integrated with a vibrator 20 which can generate high frequency vibration to the entire structure. In, this way, the placenta is kept in a naturally-inclined position at all time. In other words when the placenta is placed from the lowest energy natural position, the vibration of the device can move the placenta into the appropriate position to ensure efficient extraction of blood. Bottlenecks and clots impeding blood flow can thus be reduced. The amount of vibration is adjustable via a vibration controller.

Open-Architecture Software Control System

Figure 8:
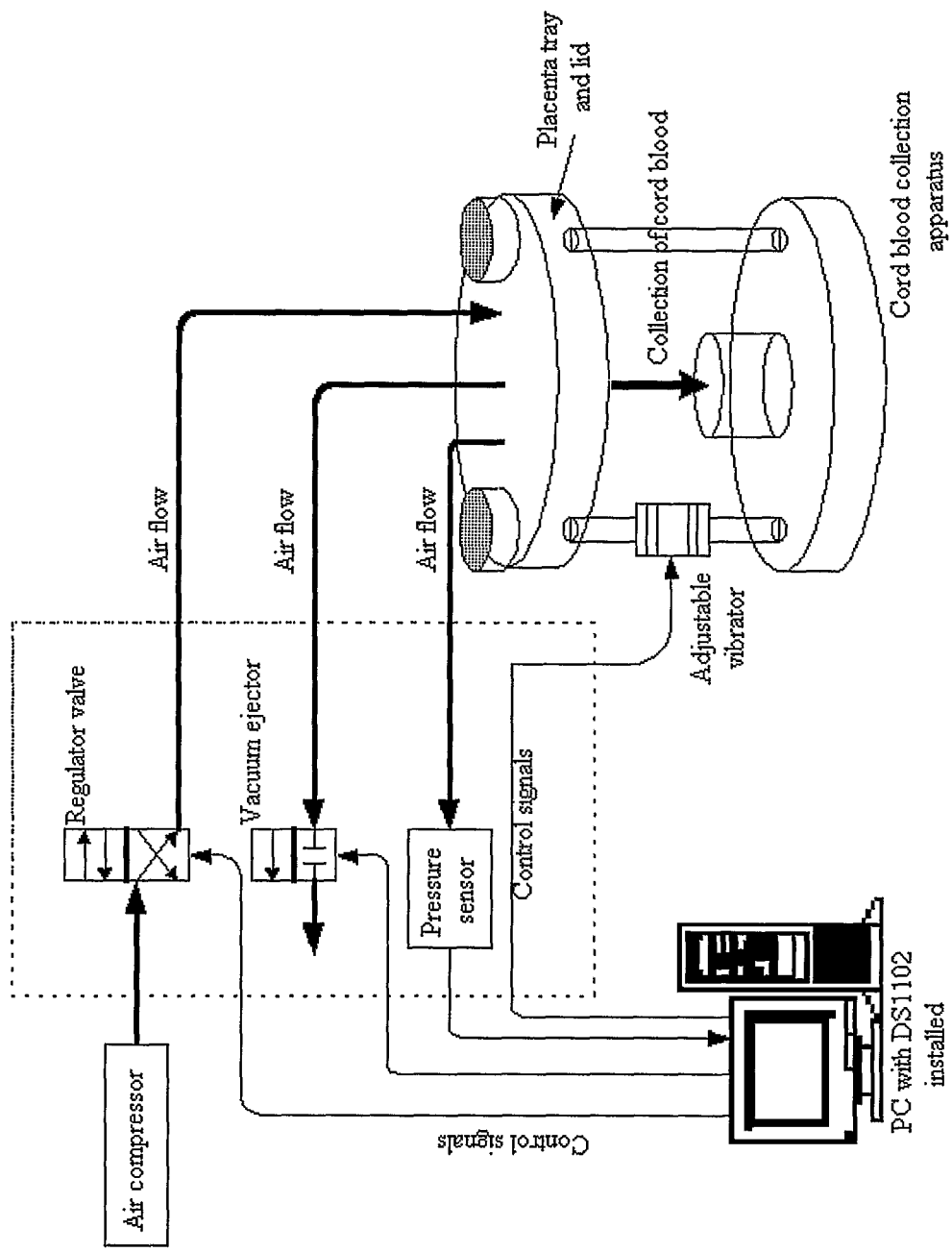
FIG. 8 is a schematic drawing of the umbilical cord blood collection apparatus including the blood collection unit as shown in FIG. 1.
Figure 9:
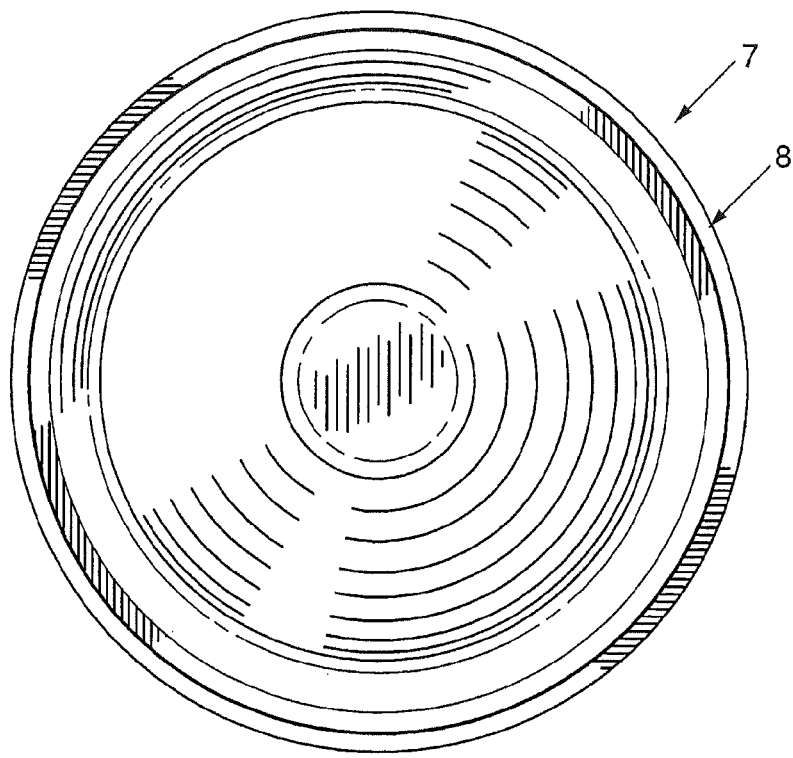
FIG. 9 is a partial perspective view of a pressure pad.
Figure 10:
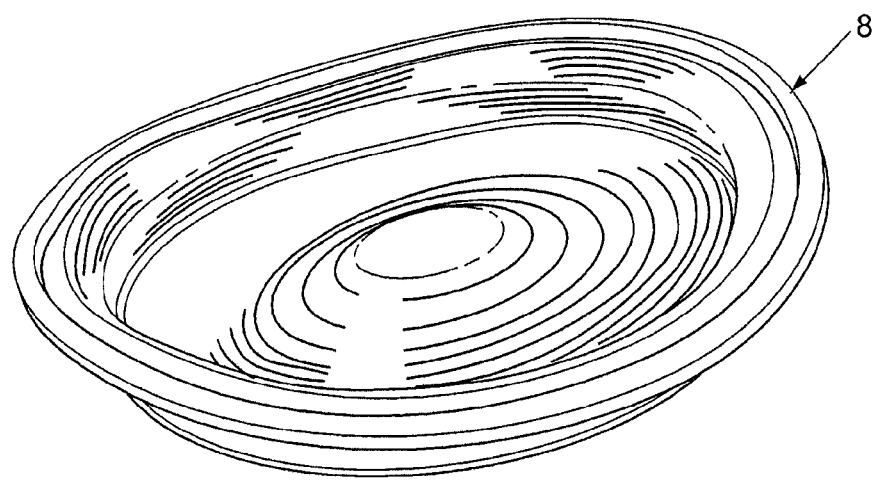
FIG. 10 is another perspective view of FIG. 9.
Figure 11:
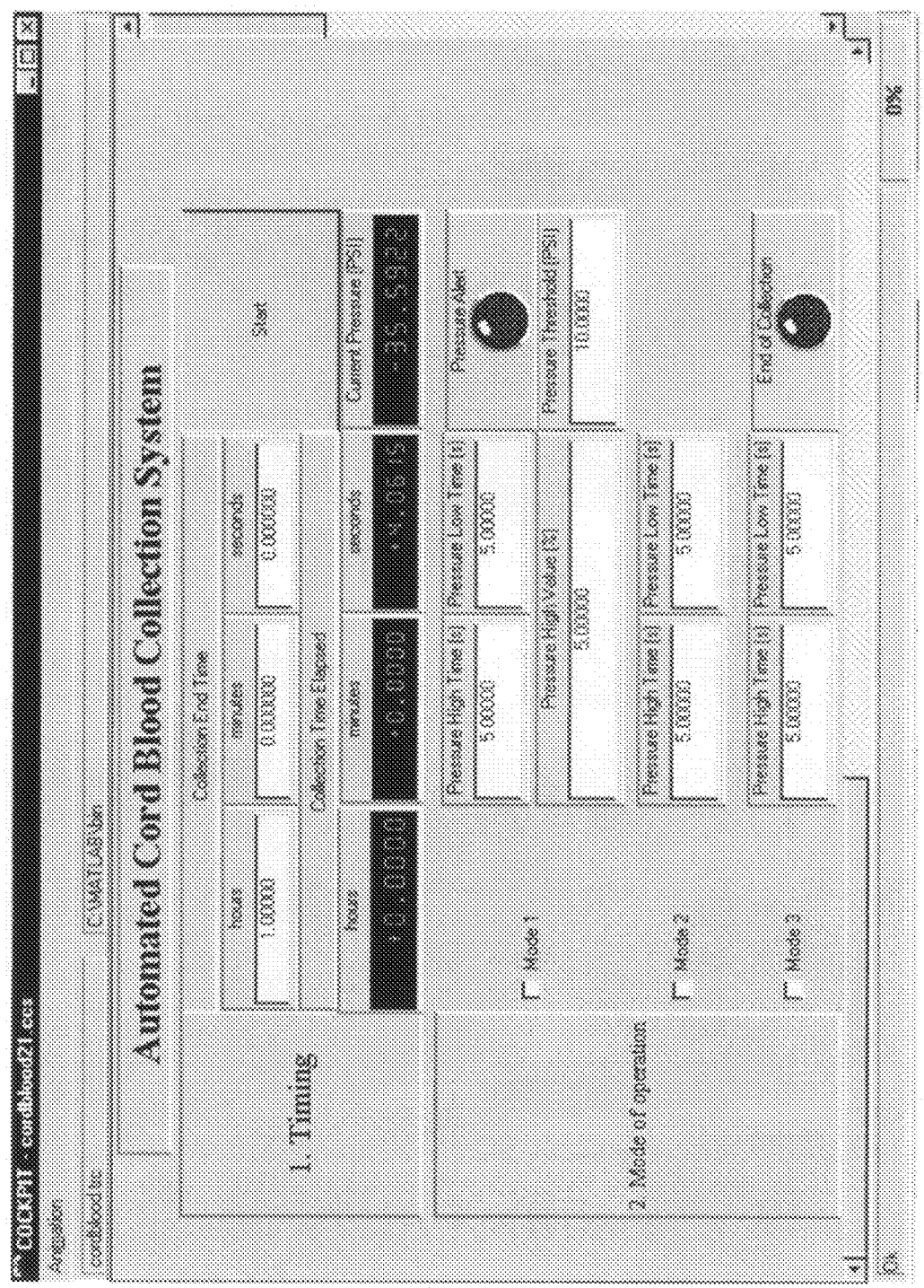
FIG. 11 shows a user interface for the control system.

The integrated full system is shown in FIG. 8 in schematic diagram form. An open-architecture software control system fulfils the overall functions of the system. It can be programmed to give different chamber pressure profiles. Closed-loop control ensures the pressure is precisely controlled to track desired profiles. Alarm and safety features can be implemented to maintain the chamber pressure within acceptable thresholds. The user interface to operate the system is shown in FIG. 11.

Test Results

The apparatus has been tested on six delivered placentas. The average total volume of UCB collected was 58.25 ml. The device was also tested for incremental improvement. It was applied after the syringe-assisted collection procedure is exhausted. The average device yield over syringe-assisted collection was 28.6%, representing the incremental volume over total volume collected.

Further Advantages

These four primary components are modular in nature so that each can be modified or replaced, while the other components remain in use. This feature facilitates repeated operations using the same device. Collectively, the four components form an electromechanical apparatus which is able to manipulate the placenta via a combination of high frequency vibration and controlled pneumatic pressure, to maximise the flow of blood from the placenta to a collection tube. In addition, all the key components which may be directly or indirectly in contact with the placenta can be readily sterilised and are also designed to filter contaminants from the collected blood. A person skilled in the art will also recognise that components of the device are preferably provided as pre-sterilised components to minimise contamination by pathogens. While some materials were given for certain components (eg stainless steel) for the pressure chamber, the person skilled in the art will appreciate that the present invention is not limited to such materials and that other materials may also be suitable for use. Accordingly, appropriate means of sterilising these components (eg by gamma or ultra-violet light irradiation, exposure to ethylene oxide, chemical disinfectants or steam autoclaving) can be used.

The foregoing description of the preferred embodiment of the invention has been presented for purposes of illustration and description. It is not intended to be exhaustive or to limit the invention to the precise forms disclosed, since many modifications or variations thereof are possible in the light of the above teaching. All such modifications and variations are within the scope of the invention. The embodiments described herein were chosen and described in order best to explain the principles of the invention and its practical application, thereby to enable others skilled in the art to utilise the invention in various embodiments and with various modifications as are suited to the particular use contemplated thereof. It is intended that the scope of the invention be defined by the claims appended hereto, when interpreted in accordance with the full breadth to which they are legally and equitably suited.

A person skilled in the art will recognise that the invention may be readily modified to accommodate umbilical cord excised or detached from the placenta. Instead of a placenta tray to hold or secure the umbilical cord, a tray with a shallow trough or two raised parallel supports can be used to support the umbilical cord. Under one embodiment of the present invention, the extraction and collection of umbilical cord blood may be carried out for an umbilical cord isolated from the placenta. The isolated umbilical cord is supported in a shallow trough of suitable width and depth and held by a holding means at the maternal end of the cord. A collection means is attached to the fetal end of the cord. The trough is supported at an inclined angle from the horizontal with the maternal end of the cord at a higher level than the fetal end. A roller of suitable diameter is then placed at the top of the trough and is then rolled by hand, or is allowed to roll slowly and evenly by itself down the trough, exerting pressure on the umbilical cord from the maternal end to the fetal end and extracting the blood in the blood vessels of the umbilical cord and the blood is collected by the collection means.

The system may be as simple or as sophisticated as the user desires. For example, the invention may be practised with only one manually controlled air inlet. Similarly the vibrator may be manually switched on and the air in the pressure application lid equilibrated with atmospheric air with a manually operated release valve. The invention is thus modular with the capability of being upgraded with components for automation or downgraded to simpler components as desired.

The person skilled in the art will appreciate that the preferred embodiment of one aspect of the present invention is a device for extracting and collecting blood from a delivered placenta comprising a means to define a compartment to locate and support a delivered placenta and umbilical cord said compartment including a flexible membrane which can be displaced (preferably under the influence of a fluid (preferably gas) pressure differential between the compartment side and non compartment side of said membrane) to impart onto at least the placenta a pressure to encourage the displacement of fluid carried by said placenta towards the umbilical cord, said compartment including at least one outlet opening via which said umbilical cord can extend (preferably in a sealed manner) to allow the flexible membrane pressure induced flow of fluid carried by said placenta to at least in part displace from said compartment for external to the compartment collection of said fluid.

The compartment of the device includes a tray like region by which (directly or indirectly) said placenta can be supported in a manner to allow said umbilical cord to extent to said outlet opening. The compartment may be pressurized.

A flexible membrane is provided in a lidding like manner to said tray like region to define said compartment. The device may have a pressure cap is able to locate over said flexible membrane in a manner to establish diaphragm pump like relationship with said compartment, the pressure cap forming a pressurisable enclosure to the opposite side of said flexible membrane to said tray side of said flexible membrane. The pressure cap may be rigid. The tray may be rigid.

The person skilled in the art will also appreciate that the preferred embodiment of another aspect of the present invention is UCB collection system for collection of blood from a delivered placenta, including (a) means for placenta and umbilical cord placement, (b) means for air-sealant and holding the placenta in place, (c) means for the application of a uniform and distributed pneumatic air pressure across the maternal surface of the placenta according to a desired pressure profile, (d) means for generating vibration of (a), (b) and (c), and (e) means for overall control of the system.

The placenta placement means of the system is of a preferably mildly cone-shaped modular element on which the placenta sits and a venturi which preferably uses a plastic component to direct the umbilical cord to a collection point.

The venturi also acts as a hard mechanical filter against contaminated blood from the surface of the placenta. The air-sealant and placenta holding means comprises of a silicone pressure pad preferably of a varying thickness Under the system of the present invention, the air sealant and placenta holding means has an integral sealing ring snapped into position above the placenta, the holding means seals the air chamber, keeps the placenta in position and evenly distributes pneumatic pressure on the placenta from the periphery towards the umbilical cord at the centre. The pneumatic pressure application means comprises of an airtight chamber into which air from a compressed air source is able to be admitted in a controlled manner, thus inducing a pneumatic pressure on the pressure pad.

The vibration generation means of the system comprises of a vibrator attached to a structure holding or supporting (a) and (b) and (c), to induce a high frequency vibration therein, thus keeping placenta in a natural positioning and reducing bottlenecks and clots to blood flow.

The control means of the system comprises an open-architecture software control system which generates desired pressure profiles, controls the chamber pressures to track these profiles precisely and which may provide alarm and relief measures.

The invention claimed is:

1. A device for extracting and/or collecting biological fluid from a delivered placenta and/or umbilical cord, the device comprising:
    a compartment to contain and/or support the placenta and/or umbilical cord;
    a pressure application lid connectable to the compartment, the pressure application lid comprising at least one inlet interface to a pressure source, at least one inlet interface to a pressure gauge, and at least one outlet interface; and
    a biological fluid collection means; and
    a pressure transmitting means comprising a pressure pad having a variable thickness so as to radially distribute pressure across the placenta in a direction from a periphery of the placenta to a centre of the placenta, the pressure pad being preformed with a double concave surface to its downward or inward side across the pressure pad with an integral peripheral sealing ring protruding therefrom, and with a wall thickness that is thicker at outer regions than at centre regions.

2. The device according to claim 1, wherein the pressure source is a gas or liquid source.

3. The device according to claim 1, wherein the at least one outlet interface is connected to a vacuum pump.

4. The device according to claim 1, wherein the fluid collection means further comprises umbilical cord positioner.

5. The device according to claim 1, wherein the fluid collection means further comprises a venturi.

6. The device according to claim 5, wherein the venturi further comprises absorbent material.

7. The device according to claim 1, further comprising means for applying vibration to the placenta and/or umbilical cord.

8. The device according to claim 7, wherein the means for applying vibration is a vibrator.

9. A device for extracting and/or collecting biological fluid from a delivered placenta and/or umbilical cord, the device comprising:
    a compartment to contain and/or support the placenta and/or umbilical cord;
    a pressure transmitting means, wherein the pressure transmitting means comprises a pressure pad having a variable thickness so as to radially distribute pressure across the placenta in a direction from a periphery of the placenta to a centre of the placenta, the pressure pad being preformed with a double concave surface to its downward or inward side across the pressure pad with an integral peripheral sealing ring protruding therefrom, and with a wall thickness that is thicker at outer regions than at centre regions; and
    a biological fluid collection means.

10. A system for extracting and/or collecting biological fluid from a delivered placenta and/or umbilical cord, the system comprising:
    an extraction and/or collection device according to claim 1, and a pressure control means.

11. The system according to claim 10, wherein the pressure control means comprises:
    at least one computing device with control software; and
    at least one electromechanical device for controlling inlet air into a pressure application lid, the pressure application lid connectable to the compartment.

12. The system according to claim 10, wherein the pressure control means further comprising at least one electromechanical device for sensing air pressure within the pressure application lid.

13. The system according to claim 10, wherein the pressure control means further comprising at least one electromechanical device for releasing pressure within the pressure application lid.

14. The system according to claim 10, wherein the pressure control means further comprising at least one control means for a vibrator.

15. A device for extracting and/or collecting biological fluid from a delivered placenta and/or umbilical cord, the device comprising:
    a compartment to contain and/or support the placenta and/or umbilical cord;
    a pressure transmitting means, wherein the pressure transmitting means comprises a pressure pad having a variable thickness so as to radially distribute pressure across the placenta in a direction from a periphery of the placenta to a centre of the placenta, the pressure pad being preformed with a double concave surface to its downward or inward side across the pressure pad with an integral peripheral sealing ring protruding therefrom, and with a wall thickness that is thicker at outer regions than at centre regions;

a means for applying vibration; and a fluid collection means.

16. The device according to claim 15, wherein the means for applying vibration is a vibrator.

17. The device according to claim 15, wherein the means for applying vibration comprises keeping the placenta and/or umbilical cord in a naturally inclined position.

18. A device for extracting and/or collecting biological fluid from a delivered placenta and/or umbilical cord, the device comprising an extraction and/or collection device according to claim 15, and a pressure control means.

19. A system for extracting and/or collecting biological fluid from a delivered placenta and/or umbilical cord, the system comprising:

an extraction and/or collection device according to claim 9, and a pressure control means.

20. The system according to claim 19, wherein the pressure control means comprises:

at least one computing device with control software; and at least one electromechanical device for controlling inlet air into a pressure application lid, the pressure application lid connectable to the compartment.

21. The system according to claim 19, wherein the pressure control means further comprising at least one electromechanical device for sensing air pressure within the pressure application lid.

22. The system according to claim 19, wherein the pressure control means further comprising at least one electromechanical device for releasing pressure within the pressure application lid.

23. The system according to claim 19, wherein the pressure control means further comprising at least one control means for a vibrator.

* * * * *